US010967166B2

(12) United States Patent
Rebecca et al.

(10) Patent No.: US 10,967,166 B2
(45) Date of Patent: Apr. 6, 2021

(54) NIPPLE AREOLA COMPLEX STENCIL

(71) Applicant: Mayo Foundation for Medical Education and Research, Rochester, MN (US)

(72) Inventors: Alanna M. Rebecca, Cave Creek, AZ (US); Solomon M. Azouz, Scottsdale, AZ (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 195 days.

(21) Appl. No.: 16/319,987

(22) PCT Filed: Jul. 26, 2017

(86) PCT No.: PCT/US2017/043849
§ 371 (c)(1),
(2) Date: Jan. 23, 2019

(87) PCT Pub. No.: WO2018/022691
PCT Pub. Date: Feb. 1, 2018

(65) Prior Publication Data
US 2019/0262596 A1 Aug. 29, 2019

Related U.S. Application Data

(60) Provisional application No. 62/366,843, filed on Jul. 26, 2016.

(51) Int. Cl.
*B41N 1/24* (2006.01)
*B41M 1/12* (2006.01)
(Continued)

(52) U.S. Cl.
CPC ....... *A61M 37/0076* (2013.01); *A61B 5/0091* (2013.01); *A61F 2/52* (2013.01);
(Continued)

(58) Field of Classification Search
CPC ...... A45D 40/30; A45D 44/002; A61B 90/39; A61B 2090/3904; A61B 2090/3908; A61B 2090/395; B41N 1/24; B41M 1/12
(Continued)

(56) References Cited

U.S. PATENT DOCUMENTS 4,778,465 A    10/1988   Wilkins
5,816,269 A * 10/1998   Mohammed ........... A45D 40/30
                                                            132/319

(Continued)

OTHER PUBLICATIONS

Pauchot et al., "Stencil technique for areola tattooing. A simple solution for quickly performed, homogeneous tattoos with regular edges", JPRAS Open, vol. 3, Mar. 1, 2015, pp. 10-12.

Boccola, M.A.; et al. (2010). Surgical correction and reconstruction of the nipple-areola complex: Current review of techniques. Journal of Reconstructive Microsurgery, 26(9):589-600.

(Continued)

*Primary Examiner* — Leslie J Evanisko

(57) ABSTRACT

Embodiments of the invention include a breast nipple areola complex tattoo stencil comprising first, second and third stencil sections. The first stencil section defines an areola area. The second stencil section defines a nipple area and tubercle areas. One or more registration elements on the first and/or second stencil sections enable registration of the second stencil section to the first stencil section. The third stencil section defines one or both of a nipple shading area and a nipple highlight area. One or more registration elements on the third and/or second stencil sections enable registration of the third stencil section to the second stencil section.

20 Claims, 3 Drawing Sheets

(51) Int. Cl.
*A61M 37/00* (2006.01)
*A61B 5/00* (2006.01)
*B41K 1/32* (2006.01)
*A61F 2/52* (2006.01)

(52) U.S. Cl.
CPC ............... *B41K 1/32* (2013.01); *B41M 1/12* (2013.01); *B41N 1/24* (2013.01); *A61F 2002/526* (2013.01); *A61M 2207/00* (2013.01); *A61M 2210/1007* (2013.01)

(58) Field of Classification Search
USPC .......... 101/114, 115, 127; 434/100; 132/285, 132/319
See application file for complete search history.

(56) References Cited

U.S. PATENT DOCUMENTS

| | | | |
|---|---|---|---|
| 6,207,874 | B1 | 3/2001 | Felton et al. |
| 6,314,315 | B1 | 11/2001 | Hung et al. |
| 6,349,640 | B1* | 2/2002 | Takebe ............... B41M 1/12 101/115 |
| 7,566,344 | B2 | 7/2009 | Hansen |
| 2006/0249173 | A1* | 11/2006 | Lawson ............... A45D 40/30 132/319 |
| 2011/0174172 | A1* | 7/2011 | Swisher ............... B41F 15/04 101/127 |
| 2014/0216282 | A1* | 8/2014 | Allen ............... B41N 1/248 101/115 |
| 2015/0025628 | A1 | 1/2015 | Langer |
| 2015/0114420 | A1 | 4/2015 | Gafni |

OTHER PUBLICATIONS

Bykowski, M.R.; et al. (2017). Nipple-areola complex reconstruction improves psychological and sexual well-being in women treated for breast cancer. Journal of Plastic, Reconstructive & Aesthetic Surgery, 70:209-214.
Goh, S.C.J.; et al. (2011). Patient satisfaction following nipple-areolar complex reconstruction and tattooing. Journal of Plastic, Reconstructive & Aesthetic Surgery, 64:360-363.
Halvorson, E. G.; et al. (2014). Three-dimensional nipple-areola tattooing: A new technique with superior results. Plast. Reconstr. Surg. 133:1073-1075.
International Preliminary Report on Patentability issued in PCT/US2017/043849, dated Feb. 7, 2019, 7 pages.
International Search Report and Written Opinion of the PCT/US2017/043849, dated Nov. 8, 2017, 10 pages.
Jabor, M.A.; et al. (2002). Nipple-areola reconstruction: satisfaction and clinical determinants. Plast. Reconstr. Surg., 110:457-463.
Kummerow, K. L.; et al. (2015). Nationwide trends in mastectomy for early-stage breast cancer. JAMA Surg., 150 (1):9-16.
NIH National Cancer Institute (2012). 2012 Breast Cancer Statistics. Available at: https://www.cancer.gov/types/breast/risk-fact-sheet. Accessed Feb. 10, 2018.
Richter, D.F.; et al. (2004). Comparison of the nipple projection after reconstruction with three different methods. Handchir Mikrochir Plast Chir, 36:374-378, in German with English Abstract.
Spear, S. L.; et al. (1995). Long-term experience with nipple-areola tattooing. Ann. Plast. Surg., 35:232-236.
Zhong, T.; et. al. (2009). Surgical outcomes and nipple projection using the modified skate flap for nipple-areolar reconstruction in a series of 422 implant reconstructions. Ann. Plast. Surg., 62:591-595.

* cited by examiner

NIPPLE AREOLA COMPLEX STENCIL

CROSS-REFERENCE TO RELATED APPLICATION

This application is a national phase application of PCT Application No. PCT/US2017/043849, internationally filed on Jul. 26, 2017, entitled, NIPPLE AREOLA COMPLEX STENCIL, which claims the benefit of Provisional Application No. 62/366,843, filed Jul. 26, 2016, entitled, NIPPLE AREOLA COMPLEX STENCIL, both of which are incorporated herein by reference in their entireties.

FIELD OF THE INVENTION

The invention relates generally to devices and methods useful in connection with anatomic cosmetic and reconstruction surgical procedures. Embodiments of the invention include stencils and methods for tattooing anatomic structures, such as nipple areola complex structures in connection with breast reconstruction surgical procedures.

BACKGROUND OF THE INVENTION

The nipple areolar complex (NAC) is comprised of the nipple and the areola. The areola contains Montgomery's Tubercles which are sebaceous glands that appear as pale mounds. The areolar skin, which has a darker pigmentation than the surrounding skin, is anchored to the underlying breast with circular muscle fibers. These muscle fibers create a contrast of color variation on the overlying pigmented skin.

Mastectomy as a treatment for breast cancer commonly involves removal of the NAC. Following implant or autologous breast reconstruction, the NAC can be reconstructed. Tattooing can be performed to create the appearance of the areola and nipple. Shading and coloring can be used to create the appearance of a three dimensional structure. An actual three dimensional structure mimicking a nipple can be created by local flaps and fat grafting a mound, and the three dimensional structure can be tattooed. Color variations of the areola are sometimes recreated by tattooing alternating colors in concentric circles. These tattooing procedures are often done free-hand. Templates having circular openings (e.g., that are cut from adhesive-backed dressings) are sometimes used in connection with the nipple tattooing procedures (e.g., to define the areola).

There remains a continuing need for improved methods and devices for cosmetic and reconstruction surgery. Devices and methods that can enhance the appearance and efficacy of anatomic structures tattooed on a patient are desired. Such devices and methods for breast reconstruction procedures would be particularly useful.

SUMMARY

Embodiments of the invention include a method for tattooing a nipple areolar complex on a breast. The method comprises placing a first stencil member defining an areola area on a patient, and tattooing an areola area on the patient using the areola area of the first stencil member as a guide. A second stencil member defining a nipple area is placed on the patient and registered to the first stencil member. A nipple area is tattooed on the patient using the second stencil member as a guide. In embodiments, placing the second stencil member on the patient further includes placing a second stencil member further defining tubercle areas, and the method further includes tattooing tubercle areas on the patient using the second stencil member as a guide. Embodiments further comprise placing a third stencil member defining one or both of a nipple shading area and a nipple highlight area on the patient, registering the third stencil member to the second stencil member, and tattooing one or both of the nipple shading area and the nipple highlight area on the patient using the third stencil member as a guide.

DESCRIPTION OF THE INVENTION

Figure 1:
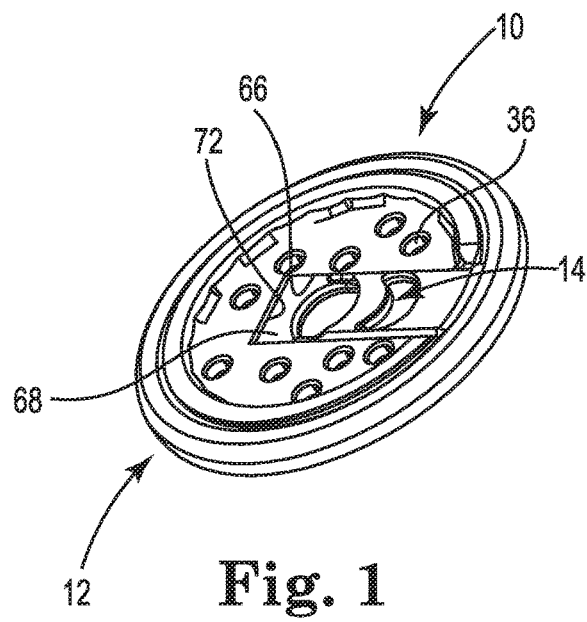
FIG. 1 is an isometric front-side view of a nipple areola complex (NAC) tattoo stencil in accordance with embodiments of the invention.
Figure 2:
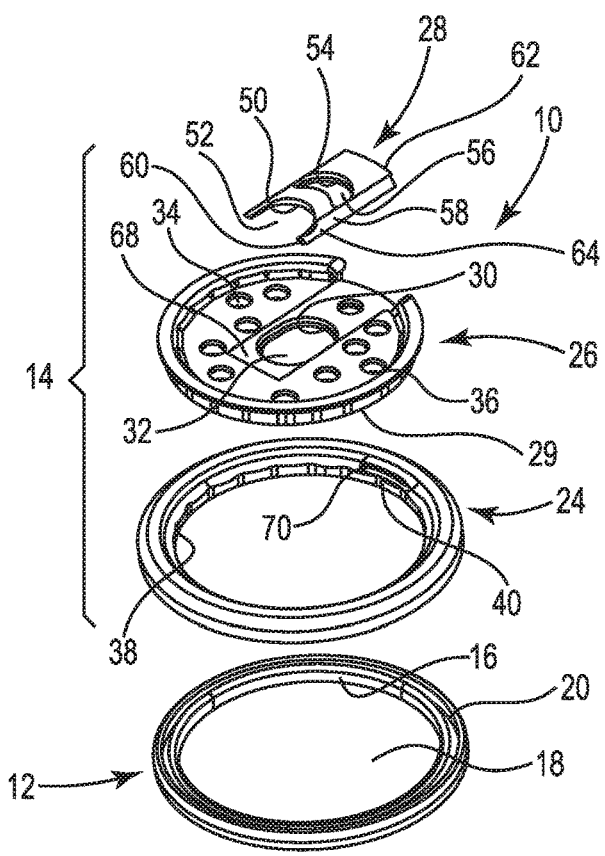
FIG. 2 is an exploded view of the stencil shown in FIG. 2.
Figure 3A:
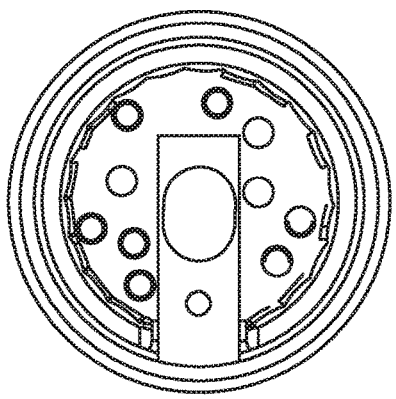
FIGS. 3A and 3B are front-side and back-side (i.e., breast-facing) views, respectively, of the stencil shown in FIG. 1, with the highlight/shading member removed.
Figure 3B:
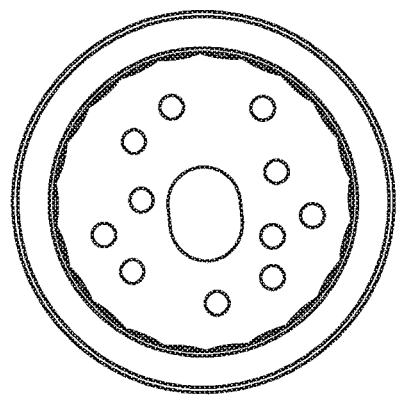

A nipple areola complex (NAC) tattoo stencil 10 in accordance with embodiments of the invention is illustrated in FIGS. 1, 2, 3A, 3B, 4A, 4B, 5A and 5B. As shown, stencil 10 includes a first or areola section 12 and a second or nipple section 14. The areola section 12 can be used as a stencil or template on a reconstructed breast to tattoo an areola. The nipple section 14 is used as a stencil or template to tattoo a nipple that is positionally registered to the tattooed areola. In embodiments, the nipple section 14 can also be configured for use as a stencil or template to tattoo other positionally registered structures on the areola, such as Montgomery's Tubercles and/or effects such as shading and highlights that provide an enhanced three-dimensional appearance to the nipple.

Areola section 12 is ring-shaped in the illustrated embodiment, and has an annular inner edge surface 16 that defines an areola opening 18. Inner edge surface 16 also provides a registration mating structure in connection with the nipple section 14. Embodiments of the first or front-side surface of the areola section 12 have a guide slot or recess 20 that can be used during the tattooing process as described below.

The illustrated embodiment of nipple section 14 includes an adapter 24, nipple/tubercle member 26 and shading member 28. Nipple/tubercle member 26 is disk-shaped in the illustrated embodiment, and has an annular outer edge surface 29, an interior edge surface 30 that defines a nipple opening 32, and a plurality of interior edge surfaces 34 that define tubercle openings 36. As shown, the tubercle openings 36 are spaced around the nipple opening 32. Adapter 24 is a ring-shaped device in the embodiment shown, and has a wall 38 with an outer surface (not visible in the drawings) that mates with the annular inner edge surface 16 of the areola section 12. An inner edge surface 40 of the adapter wall 38 mates with the outer edge surface 29 of the nipple/tubercle member 26. The mating structures and surfaces of the areola section 12, adapter 24 and nipple/tubercle member 26 function as registration structures to register the nipple/tubercle member with respect to the areola section 12 (i.e. to cause the nipple opening 32 and tubercle openings 36 to be positioned at desired locations with respect to the areola opening 18).

Shading member 28 (which is optional in embodiments) has an edge surface 50 that defines a nipple/highlight opening 52, and an edge surface 54 that defines a shading opening 56. In the embodiment shown, the edge surface 50 defines a generally semicircular area of the nipple/highlight opening area 52, and the shading opening 56 defines a crescent-shaped shading opening 56. The shading member 28 is configured to be moved between and located at first and second positions on the nipple/tubercle member 26. In the illustrated embodiment, the shading member 28 moves within a recess 68 in the nipple/tubercle member 26. The movement and positioning of the shading member 28 are facilitated by side walls 58 and end wall portions 60 and 62. Side walls 58 have outer surfaces 64 that mate with inner walls 66 of the recess 68 in the nipple/tubercle member 26, and enable the shading member 28 to slide between the first and second positions.

Figure 4A:
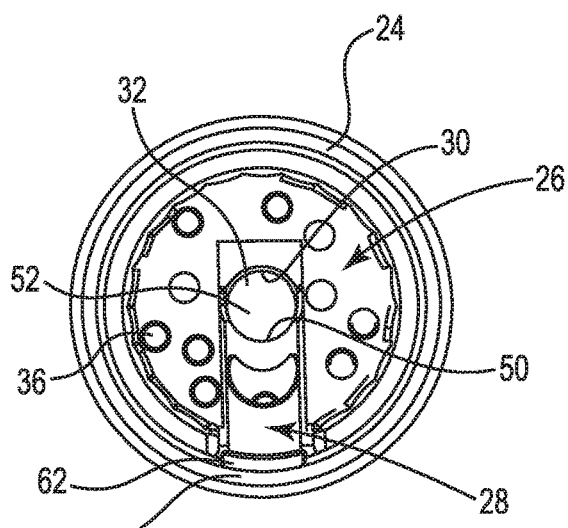
FIGS. 4A and 4B are front-side and back-side views, respectively, of the stencil shown in FIG. 1, with the highlight/shading member at a first position.
Figure 4B:
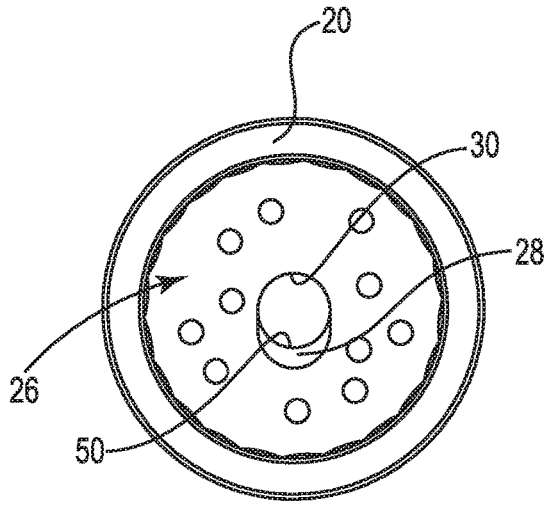
Figure 5A:
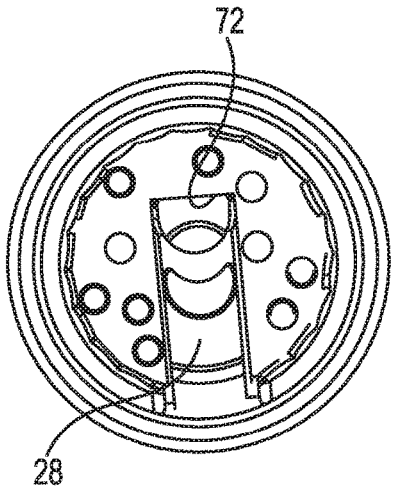
FIGS. 5A and 5B are front-side and back-side views, respectively, of the stencil shown in FIG. 1, with the highlight/shading member at a second position.
Figure 5B:
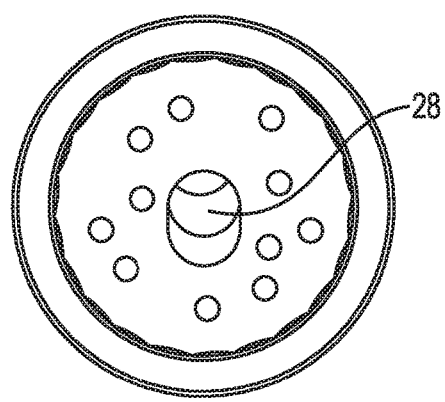

FIGS. 4A and 4B show the shading member 28 in a first or open position, with the end wall portion 62 engaged with a lip 70 on the adapter 24. As shown in FIGS. 4A and 4B, when the shading member 28 is in the first position, the edge surface 50 cooperates with the edge surface 30 of the nipple/tubercle member 26 to define a generally circular nipple area within the nipple opening area 32 of the nipple/tubercle member 26 and the nipple/highlight opening area 52 of the shading member. FIGS. 5A and 5B show the shading member 28 in a second or closed position, with the end wall portion 60 engaged with an edge wall surface 72 of the recess 60 in the nipple/tubercle member 26. As shown in FIGS. 5A and 5B, when the shading member 28 is in the second position, the edge surface 50 cooperates with the edge surface 30 of the nipple/tubercle member 26 to define a generally crescent shaped nipple highlight area within and adjacent a top edge of the nipple opening area 32 of the nipple/tubercle member 26 and the nipple/highlight opening area 52 of the shading member. When in the second position, the shading member 28 also locates the shading opening 56 within and adjacent a bottom edge of the nipple opening area 32 of the nipple/tubercle member 26.

Figure 6A:
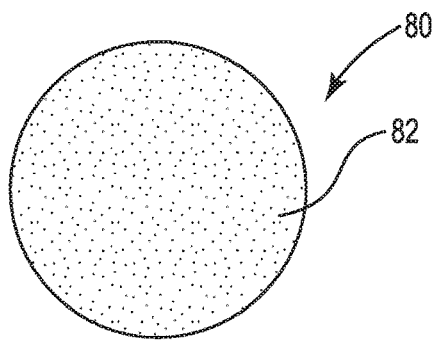
FIGS. 6A-6D illustrate a sequence of NAC structures that can be tattooed using the stencil shown in FIG. 1, with FIG. 6A illustrating the completed NAC structure.
Figure 6B:
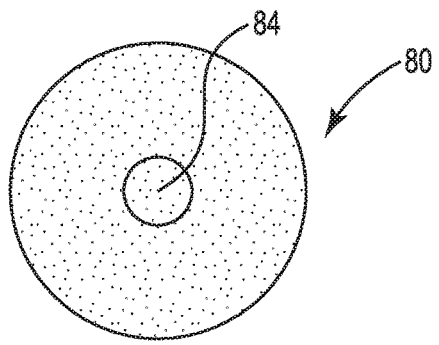
Figure 6C:
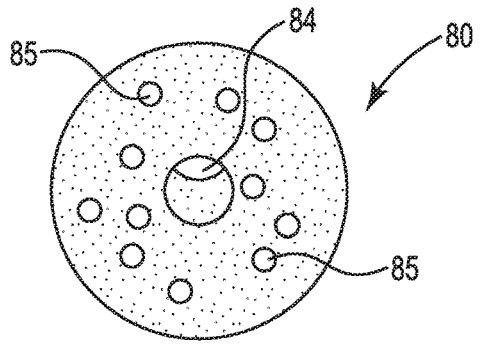
Figure 6D:
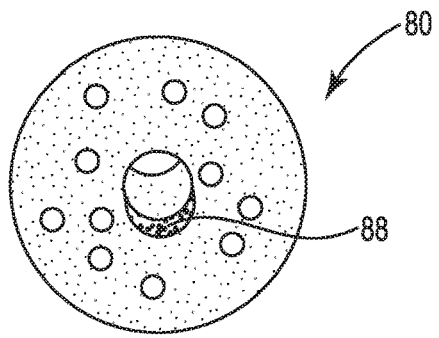

FIGS. 6A-6D illustrate a sequence of steps by which a NAC tattoo 80 can be tattooed on a reconstructed breast using embodiments of the stencil 10. In embodiments, and as shown in FIG. 6A, an areola tattoo 82 can (but need not) be applied to the breast first. The areola tattoo 82 can be applied using the areola section 12 (e.g., edge surface 16 defining the areola opening 18) as a guide. In embodiments, a first or background color tone can be used for the areola tattoo 82. For example, with the nipple/tubercle section 14 removed from the areola section 12, the areola section can be placed on the breast and the areola tattoo 82 can be applied in the areola opening 18. The areola section 12 can be releasably secured to the breast during the application of the areola tattoo 82, for example by adhesive on the bottom, breast-facing side of the areola section. In other embodiments, a layer of adhesive material (not shown) such as transparent 3M™ Tegaderm™ dressing can be applied over the top and beyond the peripheral edges of the areola section 12 to secure the areola section to the breast. The section of the adhesive material over the areola opening 18 can be cut away by a scalpel using recess 20 as a guide and barrier, and the cut away material removed to provide access to the areola opening 18. In embodiments, the areola section 12 can be packaged in a sterile package (not shown) having the layer of adhesive material and a protective release liner over the adhesive. In these embodiments, after removing the areola section 12 from the package, the release liner can be removed from the layer of adhesive material before applying and using the areola section in the manner described above.

In embodiments, after the areola tattoo 82 is applied, the nipple section 14 can be mounted to the areola section 12, and the shading member 28 moved to the first or open position. A nipple tattoo 84 can then be applied, using the nipple/tubercle member 26 and shading member 28 (e.g., edge surfaces 30 and 50 defining the nipple area within the nipple opening area 32) as a guide. In embodiments, the nipple tattoo 84 is applied using a second color tone that is lighter than the first color tone of the areola tattoo 82.

Tubercle tattoos 85 are applied in embodiments using the nipple/tubercle member 26 (e.g., edge surfaces 34 defining tubercle openings 36) as guides. In embodiments, the tubercle tattoos 85 are applied using a third color tone that is lighter than the second color tone of the nipple tattoo 84.

In embodiments where it is desired to apply a nipple highlight tattoo 86 and/or shading tattoo 88, the shading member 28 can be moved to the second or closed position. The nipple highlight tattoo 86 can be applied using the nipple/tubercle member 26 and shading member 28 (e.g., edge surfaces 30 and 50 defining the nipple highlight area within the nipple opening area 32) as a guide. In embodiments, the nipple highlight tattoo 86 is applied using the third color tone. The nipple shading area tattoo 88 can be applied using the shading member 28 (e.g., edge surface 54 defining the shading opening 56) as a guide. In embodiments, the nipple shading tattoo 88 is applied using a fourth color tone that is darker than the first color tone.

Other embodiments of the invention use different color tone palates than those described above. In embodiments, the color tones can be determined electronically/optically by imaging colors of the associated NAC structures of the patient's pre-operative breast. Still other embodiments include more or fewer tattoo areas. For example, the stencil 10 can include additional stencil areas to enhance the visual appearance of the tattoo. In embodiments, electronic imaging can be used to determine the structures of the patient's pre-operative breast, and used to generate custom stencils 10 (e.g., by 3-D printing) having structures that provide tattoos corresponding to the patient's original NAC structures (e.g., sizes, shapes and locations of the areola, nipple and tubercles). The stencil 10 can be manufactured from plastic or other materials. Other embodiments of the invention tattoo the different NAC structures in different orders.

Although the invention has been described with reference to preferred embodiments, those skilled in the art will recognize that changes can be made in form and detail without departing from the spirit and scope of the invention. For example, stencils in accordance with embodiments of the invention can be used for other tattooing applications, such as scar camouflage, hair transplant camouflage, simulation of genitalia, simulation of anus, and other anatomical sites. Alternatively and/or in addition to the mating structures, visual alignment indicia such as lines or other marks can be located on the various sections and members of the stencil to provide the registration functionality.

The invention claimed is:
1. A breast nipple areola complex tattoo stencil, comprising:
   a first stencil section defining an areola area;
   a second stencil section defining a nipple area;

one or more registration elements on the first and/or second stencil sections, to enable registration of the second stencil section to the first stencil section;
a third stencil section defining one or both of a nipple shading area and a nipple highlight area;
one or more registration elements on the third and/or second stencil sections, to enable registration of the third stencil section to the second stencil section;
wherein the one or more registration elements on the third and/or second stencil sections includes mating structures on the second and third stencil sections, enabling the third stencil section to engage and mate with the second stencil section;
wherein the mating structures on the second and third stencil sections enable the third stencil section to slide on the second stencil section between a first position and a second position;
wherein when the third stencil section is at the first position the third stencil section provides access to the nipple area of the second stencil section, and
wherein when the third stencil section is at the second position the third stencil section registers the one or both of the nipple shading area and the nipple highlight area with respect to the nipple area of the second stencil section.

2. The stencil of claim 1 wherein the second stencil section further defines tubercle areas.

3. The stencil of claim 1 wherein the one or more registration elements include mating structures on the first and second stencil sections enabling the second stencil section to engage and mate with the first stencil section.

4. The stencil of claim 3 wherein the mating structures include:
a first diametrical surface portion on the first stencil section; and
a second diametrical surface portion on the second stencil section, wherein the second diametrical surface portion of the second stencil section engages the first diametrical surface portion of the first stencil section.

5. The stencil of claim 1 wherein the third stencil section defines both the nipple shading area and the nipple highlight area.

6. The stencil of claim 1 and further including adhesive on the first stencil section to releasably secure the first stencil section to a breast.

7. The stencil of claim 6 wherein the adhesive is on a base layer of material extending peripherally from the first stencil section.

8. The stencil of claim 7 wherein the base layer of material extends over the areola area, and the portion of the base layer of material extending over the areola area can be removed prior to use of the first stencil section.

9. The stencil of claim 8 wherein the first stencil section further includes a guide, to facilitate removal of the base layer of material extending over the areola area.

10. The stencil of claim 6 and further including a protective release layer over the adhesive.

11. A method for tattooing a nipple areolar complex on a breast, including:
placing a first stencil member defining an areola area on a patient;
tattooing an areola area on the patient using the areola area of the first stencil member as a guide;
placing a second stencil member defining a nipple area on the patient;
registering the second stencil member to the first stencil member; and
tattooing a nipple area on the patient using the second stencil member as a guide.

12. The method of claim 11 wherein:
placing the second stencil member on the patient further includes placing a second stencil member further defining tubercle areas; and
the method further includes tattooing tubercle areas on the patient using the second stencil member as a guide.

13. The method of claim 11 wherein registering the second stencil member to the first stencil member includes engaging the second stencil member to the first stencil member by mating structures.

14. The method of claim 11 and further including:
placing a third stencil member defining one or both of a nipple shading area and a nipple highlight area on the patient;
registering the third stencil member to the second stencil member; and
tattooing one or both of the nipple shading area and the nipple highlight area on the patient using the third stencil member as a guide.

15. The method of claim 14 wherein the steps of placing the second and third stencil members on the patient include placing an assembly including both the second and third stencil members on the patient.

16. The method of claim 15 wherein:
placing the assembly including the second and third stencil members on the patient includes placing an assembly having the third member that is movable between first and second positions on the second member;
tattooing the nipple area includes tattooing the nipple area when the third member is at the first position on the second member;
the method further includes moving the third member to the second position; and
tattooing one or both of the nipple shading area and the nipple highlight area when the third stencil member is at the second position.

17. The method of claim 11 and further including adhesively attaching the first stencil member to the patient.

18. The method of claim 17 wherein:
the first stencil member includes a base layer of material including a portion extending across the areola area and a portion extending peripherally from the first stencil member, and wherein at least the portion of the base layer extending peripherally from the first stencil member includes adhesive and a release layer covering the adhesive; and
adhesively attaching the first stencil member to the patient includes:
removing the base layer of material from the areola area;
removing a release layer from the adhesive on a base layer of material extending peripherally of the first stencil member; and
attaching the first stencil member to the patient using the adhesive on the portion of the base layer extending peripherally of the first stencil member.

19. The method of claim 18 wherein removing the base layer of material includes cutting the base layer using a cutting guide in the first stencil member.

20. The method of claim 11 and further including:
pre-operatively imaging the patient's nipple areolar complex;

deriving data representative of one or both of the color and shapes of any one or more of the areola, tubercles and nipples from the image; and manufacturing one or more of the stencil members using the derived data; and selecting one or more colors for the tattooing using the derived data.

\* \* \* \* \*